United States Patent [19]
Chambers et al.

[11] Patent Number: 5,847,198
[45] Date of Patent: Dec. 8, 1998

[54] PROCESS FOR THE PREPARATION OF ESTERS

[75] Inventors: Richard Dickinson Chambers; John Hutchinson, both of Durham; Julie Thomson, Preston, all of United Kingdom

[73] Assignee: F2 Chemicals Limited, United Kingdom

[21] Appl. No.: 973,677

[22] PCT Filed: Jun. 7, 1996

[86] PCT No.: PCT/GB96/01355

§ 371 Date: Dec. 12, 1997

§ 102(e) Date: Dec. 12, 1997

[87] PCT Pub. No.: WO97/00848

PCT Pub. Date: Jan. 9, 1997

[30] Foreign Application Priority Data

Jun. 20, 1995 [GB] United Kingdom .................... 9512546

[51] Int. Cl.$^6$ ..................................................... C07C 69/38
[52] U.S. Cl. .......................... 560/192; 560/156; 560/180; 560/76; 558/303

[58] Field of Search ...................................... 560/156, 192, 560/180, 76; 558/603

[56] References Cited

FOREIGN PATENT DOCUMENTS

| 103233 | 3/1984 | European Pat. Off. . |
| 4237882 | 5/1994 | Germany . |
| 46769 | 11/1991 | Japan . |
| 185878 | 10/1966 | U.S.S.R. . |
| 94/10120 | 5/1994 | WIPO . |
| 95/14646 | 6/1995 | WIPO . |

*Primary Examiner*—Paul J. Killos
*Assistant Examiner*—Rosalynd Keys
*Attorney, Agent, or Firm*—Nixon & Vanderhye

[57] ABSTRACT

A process for the preparation of an ester, especially fluorinated esters $R_1O.OC$—$CHR_2$—$CO.OR_3$, $R_1$ and $R_3$ are each independently selected from alkyl, cycloalkyl and aryl. $R_2$ is selected from hydrogen, alkyl, cycloalkyl. The method includes the steps of covering a corresponding compound of formula 2: $R_1O.OC$—$CHR_2$—$CO.OR_3$ in the presence of a base, of salt of a compound of formula 2, into corresponding compound of formula 1 by the reaction of elemental fluorine.

8 Claims, No Drawings

PROCESS FOR THE PREPARATION OF ESTERS

The present invention relates to a process for the preparation of esters, in particular of fluorinated esters of dicarboxylic acids which comprise 2-fluoro- and 2,2-difluoromalonic acid, and esters of 2-substituted-2-fluoro-malonic acids.

The use of elemental fluorine for the site specific fluorination of aliphatic compounds is rarely satisfactory due to the high reactivity of the element which leads to unspecific multiple substitution, carbon-carbon bond cleavage and oxidation. Because of the growing importance of fluorinated organic compounds in biochemical systems (R. Filler and Y. Kobayashi; Biochemical Aspects of Fluorine Chemistry; Elsevier Biomedical Press, New York, 1982.

J. T. Welch and S. Eswarakrishnan; Fluorine in Bioorganic Chemistry; John Wiley, New York, 1991) in recent years considerable effort has been devoted to finding ways of introducing fluorine into specific sites within molecules. Such molecules are valuable building blocks for the synthesis of biologically active compounds which have more complex structures. In this context, the preparation of fluoromalonic esters and difluoromalonic esters has aroused much interest since these compounds are useful intermediates in the preparation of bioactive molecules (T. Tsushima, K. Kawada, O. Shiratori and N. Uchida; Heterocycles, 1985, 1, 45). Hitherto, these compounds have been prepared by treating the alkali metal salts of malonic esters with an "electrophilic fluorinating agent" such as perchloryl fluoride (C. E. Inman, R. E. Oersterling and E. A. Tyczkowski; J Amer. Chem. Soc., 1958, 80, 6533), N-fluoro-N-sulphonamides (W E Barnette; J Amer. Chem. Soc., 1984, 106, 453), N-fluoro-2-pyridone (S. T. Purrington and W. A. Jones; J Org. Chem., 1983, 48, 761), N-fluoro-benzenesuphonimides (E. Differding and H. Ofner; Synlett., 1991, 187), N-Fluoro-pyridinium salts (with or without the addition of a Lewis acid) (T. Umemoto, S. Fukami, G. Tomizawa, K.K. Harasawa, K. Kawada and K. Tomita; J. Amer. Chem. Soc., 1990, 112, 8575), 1-alkyl-4-fluoro-1,4-diazabicyclo[2,2,2,]octane salts (G. A. Lal; J. Org. Chem., 1993, 58, 2791. R. E. Banks, N. J. Lawrence and A. L. popplewell; J. Chem. Soc., Chem. Commun., 1994, 343), N-fluoro-bis(perfluoroalkyl)sulphonimides (Z. Xu, D. D. Desmarteau and Y. Gotoh; J. Chem. Soc., Chem. Commun., 1991, 179. Z. Xu, D. D. Desmarteau and Y. Gotoh; J. Fluorine Chem., 1992, 58, 71. G. Resnati and D. D. Desmarteau; J. Org. Chem., 1991, 56, 4925), perfluoropiperidine (R. E. Banks and G. E. Williamson; Chem. Ind. (London), 1964, 1864) and acetyl hypofluorite (O. Lerman and S. Rozen; J. Org., Chem., 1983, 48, 724).

Although the treatment of alkali metal salts of malonic esters with electrophilic fluorinating agents can sometimes give high yields of the required mono- or di-fluorinated products, some of these reagents decompose fairly quickly, and the compounds from which they are made are often expensive or difficult to obtain.

Other methods for making esters of 2-fluoro- and 2,2,-difluoro-malonic acids are less direct. They are frequently inefficient, involve several steps in their synthesis or require starting materials which are expensive or difficult to obtain.

Thus, the prior art methods of preparing malonic esters are not satisfactory.

Surprisingly, we have now found a convenient and efficient process for the preparation of esters of 2-fluoro- and 2,2-difluoro-malonic acids which involves the use of elemental fluorine.

According to the present invention there is provided a process for the preparation of an ester having a formula 1:

$$R_1O.OC—CFR_2—CO.OR_3 \qquad \text{formula 1}$$

which includes the steps of converting the corresponding compound of formula 2 as follows

$$R_1O.OC—CHR_2—CO.OR_3 \qquad \text{formula 2}$$

in the presence of a base, or a salt of a compound of formula 2, into the corresponding fluorinated compound of formula 1 by reaction with elemental fluorine.

In formulae 1 and 2, $R_1$ and $R_3$ are each independently selected from alkyl, cycloalkyl and aryl. For instance, each $R_1$ and $R_3$ group may be an n-alkyl group having from 1 to 4 carbon atoms.

In formulae 1 and 2, $R_2$ is selected from hydrogen, alkyl, cyclo-alkyl, preferably $C_{1-6}$ alkyl, nitro, cyano, halogen, alkoxy, acetamido, alkoxycarbonyl, aryloxycarbonyl and aryl.

Where $R_2$ is formula 2 is hydrogen, $R_2$ in formula 1 may be fluorine. Thus, substitution by fluorine may take place at both available hydrogen atoms attached to the internal carbon atom of the molecule.

The ester of formula 2 may be added to a base before fluorination. For example, the ester of formula 2 may be added to an inorganic base such as an alkali metal hydride or alkoxide which before fluorination converts the ester into a salt in one of the ways well known to those skilled in the art.

Thus, the salt which takes part in the fluorination may have formula 3 as follows:

$$R_1O.OC—CMR_2—CO.OR_3 \qquad \text{formula 3}$$

where M is a suitable cation, eg an alkali metal, and $R_1$ to $R_3$ are as defined above.

Alternatively, a base which is not employed to convert the ester of formula 2 into a salt may be employed to promote fluorination. Such a base may be added to the reacting ester before or during addition of fluorine. Suitable bases include alkali metal halides, eg fluorides, eg sodium, potassium or caesium fluoride, organic bases such as pyridine or substituted pyridines, organic amines such as trialkylamines or Proton Sponge®.

The process according to the present invention may be carried out by passing fluorine gas into a suitably inert liquid containing the ester and base or the salt. A suitably inert organic for this process solvent would be acetonitrile. The reaction may be carried out in a vessel in which the said liquid is present or alternatively a flow stream of the liquid may be contacted with a gaseous flow of fluorine in countercurrent fashion. Typically, the process may be carried out at a temperature of from −45° C. to 80° C., preferably at a temperature from −20° C. to 30° C. and especially at a temperature from −10° C. to 15° C.

The fluorine gas employed in the process according to the present invention is preferably diluted before use by mixing with an inert gas such as nitrogen or helium. The concentration of fluorine is preferably from 1% to 50% by volume, more preferably from 2% to 25% and especially from 5% to 15%.

The ratio of fluorine to ester of formula 2 or its salt may be varied within wide limits although it is preferred that the molar ratio of fluorine to ester or salt is from 0.5:1 to 6:1, and especially from 0.8:1 to 3:1. Use of a higher ratio of fluorine to ester or salt ensures that two fluorine atoms are introduced into the molecule where required.

When fluorination is complete the fluorinated products may be isolated by purging the reaction mixture with nitrogen to remove any residual fluorine gas followed by a suitable separation process such as distillation.

The method according to the present invention surprisingly and beneficially offers a simple and convenient route to the preparation of fluorinated esters of dicarboxylic acids such as malonic acids directly from the parent unfluorinated ester using elemental fluorine.

For example, the present process provides an inexpensive and convenient synthetic route to 2-fluoro- and 2,2-difluoro-esters of malonic acid.

The method according to the present invention is further illustrated by way of example only with reference to the following Examples:

EXAMPLE 1

Preparation of diethyl 2-fluoro- and diethyl 2,2-difluoro-malonates

A solution of diethyl malonate (2.0 gm, 12.5 mmol) in dry acetonitrile (10 ml) was added over 30 min. to a suspension of degreased sodium hydride (0.3 gm., 12.5 mmol.) in dry acetonitrile (50 ml) at room temperature. Through the cooled (ca. −15° C.) white suspension of the sodium derivative was bubbled fluorine (25 mmol.) diluted to 10% in nitrogen over a period of 1 hour during which time the temperature was maintained between −20° C. and −15° C. After this treatment, the reaction vessel was purged with nitrogen and allowed to warm to room temperature (20° C.). The colourless solution was filtered and most of the solvent removed by distillation to give 1.9 gm of a pale yellow liquid. Short path length, reduced pressure distillation of 1.6 gm of this material yielded 1.45 gm of a mixture of acetonitrile, unreacted diethyl malonate, diethyl fluoromalonate ([$d_F$(CDCl$_3$)− 195.6 ppm, (d) 50.3 Hz., m/z 178], and diethyl difluoromalonate [$d_F$(CDCl$_3$)−112.7 ppm, (s), m/z 196]. The conversion was ca. 70% and the yields of the monofluoro- and difluoro-compounds were 37% and 24% respectively.

EXAMPLE 2

Preparation of diethyl 2-fluoro- and diethyl 2,2-difluoro-malonates

A reaction similar to that described in Example 1 was carried out in which 25 mmol. diethyl malonate was treated successively with 56 mmol. sodium hydride and 75 mmol. fluorine. The conversion was 94% and the yields of diethyl 2-fluoro- and diethyl 2,2-difluoro-malonates were 14% and 37% respectively.

EXAMPLE 3

Reaction of Diethyl Malonate and Fluorine without Base

To demonstrate the importance of treating the diester with base, fluorine (50 mmol, 10% in nitrogen) was passed through a solution of diethyl malonate (4 gm, 25 mmol) in acetonitrile over 1 hour 30 min with no base present. After purging with nitrogen, the nmr spectrum of the reaction product showed the complete absence of any fluorinated derivatives of diethyl malonate.

EXAMPLE 4

Preparation of diethyl 2-fluoro-2-methylmalonate

By a similar method to that described in Example 1, diethyl methylmalonate (4.35 gm, 25 mmol) was dissolved in acetonitrile (10 ml) and treated successively with degreased sodium hydride (0.6 gm, 25 mmol), 1 eq) in dry acetonitrile (40 ml) and fluorine (1.9 gm, 50 mmol, 2 eqs) (10% in nitrogen). After this treatment, the reaction mixture was purged with nitrogen, allowed to warm to room temperature (20° C.) and filtered. Most of the solvent was removed by distillation to give a pale yellow liquid (4.7 gm). Short path length reduced pressure distillation of 3. 6 gm of this material gave a mixture (2.8 gm) of acetonitrile starting material and diethyl 2-fluoro-2-methylmalonate [$d_F$(CDCl$_3$) −158.0 ppm, (q), 22.2 Hz; m/z (CI, NH$_3$) 210 (100%)]. Conversion was 74% and the yield of diethyl 2-fluoro-2-methylmalonate was 60%.

EXAMPLE 5

Preparation of diethyl 2-fluoro-2-methylmalonate

Under an atmosphere of nitrogen, diethylmethylmalonate (4.35 gm), 25 mmol) dissolved in acetonitrile (10 ml) was added to a suspension of sodium ethoxide (96%, 1.8 gm, 25 mmol) in acetonitrile (40 ml). The reaction mixture was heated to about 45° C. for 20 mins and then cooled to −20° C. at which temperature fluorine (50 mmol) diluted with nitrogen to 10% was bubbled through the reaction mixture over a period of 1 hour 40 mins. After this treatment, the reaction mixture was purged with nitrogen, allowed to warm to room temperature (20° C.) and filtered. Most of the solvent was removed from the filtrate by distillation to yield a pale yellow liquid (5.1 gm). Short path length, reduced pressure distillation of 4.7 gm of this material afforded of a mixture (4.1 gm) of solvent, starting material and 2-fluoro-2-methylmalonate. Conversion was 40% and the yield of 2-fluoro-2-methylmalonate was 60%.

EXAMPLE 6

Preparation of diethyl 2-butyl-2-fluoromalonate

By a similar method to that described in Example 1, diethyl 2-butylmalonate (5.40 gm, 25 mmol) was dissolved in acetonitrile (10 ml) and added to a suspension of degreased sodium hydride (0.75 gm, 32.25 mmol) in acetonitrile (40 ml) and treated with fluorine (ca 2.2 gm, 57 mmol, 2.3 eqs) (10% nitrogen). After this treatment, the reaction mixture was purged with nitrogen, allowed to warm to room temperature and filtered. Most of the solvent was removed to give a yellow liquid (6.2 gm). Short path length, reduced pressure distillation of 4.8 gm of this material gave 4.2 gm of a mixture of acetonitrile, starting material and diethyl 2-butyl-2-fluoromalonate [$d_F$(CDCl$_3$)−167.7 ppm (t), ca 22.8 Hz); m/z (CI, NH$_3$) 252 (100%, 234+18)]. A conversion of 65% was obtained and the yield of diethyl 2-butyl-2-fluoromalonate was 70%.

EXAMPLE 7

Preparation of dimethyl 2-fluoro-2-methoxymalonate

By a similar method to that described in Example 1, dimethyl-2-methoxymalonate (4.05 gm, 25 mmol) was dissolved in acetonitrile (10 ml) and added to a suspension of degreased sodium hydride (0.75 gm, 31.25 mmol 1.25 eqs) in acetonitrile (40 ml). The mixture was heated to a temperature of from 40° C. to 45° C. for about 1 hour. After cooling, fluorine (ca 2.7 gm, 71.42 mmol, 2.86 eqs) (10% in nitrogen) was bubbled through the suspension at a temperature of about −10° C. over a period of 2 hr 15 min. After this treatment, the reaction mixture was purged with nitrogen, allowed to warm to room temperature and filtered. Most of the solvent was removed by distillation to give a pale yellow liquid (5.3 gm). Short path length, reduced pressure distillation of 4.2 gm of this material gave 3.6 gm of a mixture of solvent, starting material and dimethyl 2-fluoro-2-methoxymalonate [$d_F$(CDCl$_3$)–124.4(s); $d_H$ (CDCl$_3$) 3.90 ppm (s, CO$_2$Me); 3.57 (s, Ome); m/z (CI, NH$_3$)198]. Conversion was 75% and the yield of dimethyl 2-fluoro-2-methoxymalonate was 50%.

EXAMPLE 8

Preparation of diethyl 2-chloro-2fluoromalonate

By a similar method to that described in Example 1, diethyl 2-chloromalonate (4.86 gm, 25 mmol) was dissolved in acetonitrile (10 ml) and added to a suspension of degreased sodium hydride (0.75 gm, 32.25 mmol, 1.25 eqs) in acetonitrile (40 ml) and treated with fluorine (ca 1.9 gm, 50 mmol, 2 eqs) (10% in nitrogen). After this treatment, the reaction mixture was purged with nitrogen, allowed to warm to room temperature and filtered. Most of the solvent was removed by distillation to give a pale yellow liquid (5 gm). Short path length, reduced pressure distillation of 4.1 gm of this material gave 2.2 gm of a mixture of acetonitrile, starting material and diethyl 1-chloro-1-fluoromalonate ($d_F$ (CDCl$_3$)–120.8 ppm; m/z (CI, NH$_3$) 230 (13.3%, 212+18), 196 (100%)]. Conversion was 97% and the yield of diethyl 1-chloro-1-fluoromalonate was 40%.

EXAMPLE 9

Preparation of diethyl 2-fluoro-2-nitromalonate

By a similar method to that described in Example 1, diethyl 2-nitromalonate (5.13 gm, 25 mmol) was dissolved in acetonitrile (10 ml) and added to a suspension of degreased sodium hydride (0.75 gm, 32.25 mmol, 1.25 eqs) in acetonitrile (40 ml) and treated with fluorine (ca 1.90 gm, 50 mmol, 2 eqs) (10% nitrogen). After this treatment, the reaction mixture was purged with nitrogen, allowed to warm to room temperature and filtered. Most of the solvent was removed by distillation to give a pale yellow liquid (5 gm). Short path length, reduced pressure distillation of 4 gm of this material gave 3.5 gm of a mixture of acetonitrile and diethyl 2-fluoro-2-nitromalonate [$d_F$(CDCl$_3$)–127.3 ppm, (s); m/z (CI, NH$_3$) 241 (4.4%, 223+18); 196 (100%). The yield of diethyl 2fluoro-2-nitromalonate was 73% for a quantitative conversion.

EXAMPLE 10

Preparation of diethyl 2-fluoro-2-nitromalonate

In a manner similar to that described in Example 5, diethyl 2-nitromalonate (5.1 gm, 25 mmol) dissolved in acetonitrile (10 ml) was added to a suspension of sodium ethoxide (96%, 1.8 gm, 25 mmol) in acetonitrile (40 ml) over about 7 min and stood for a further 10 min to give a yellow solution. The reaction mixture was cooled to a temperature of –20° C. and fluorine (50 mmol) diluted with nitrogen to 10% was bubbled through it over a period of 2 hours. After this treatment, the reaction mixture was allowed to warm to room temperature, filtered, and most of the solvent was removed from the filtrate by distillation to yield a pale yellow liquid (6.9 gm). Short path length, reduced pressure distillation of 4.7 gm of this material afforded 4.3 gm of a mixture which was analysed by gc and nmr. Conversion was 77% and the yield of 2-fluoro-2-nitromalonate was 90%.

EXAMPLE 11

Preparation of diethyl 2-fluoro-2-nitromalonate

Fluorine (57 mmol) diluted with nitrogen to 10% was passed through a slurry of potassium fluoride (5.8 gm 100 mmol) in a solution of diethyl 2-nitromalonate (5.1 gm, 25 mmol) in acetonitrile (50 ml) at a temperature of –15° C. over a period of 2 hours. After this treatment, the reaction mixture was purged with nitrogen, allowed to warm to room temperature and filtered. Most of the solvent was removed by distillation to give 6.2 gm of a pale yellow liquid. Short path length, reduced pressure distillation of 5.6 gm of this material gave 5.2 gm distillate which was analysed by gc and nmr. Conversion was 70% and the yield of diethyl 2-fluoro-2-nitromalonate was 85%.

We claim:

1. A process for the preparation of an ester of formula 1:

R$_1$O.OC—CFR$_2$—CO.OR$_3$     formula 1 wherein:

R$_1$ and R$_3$ are each independently selected from alkyl, cycloalkyl and aryl, R$_2$ is selected from hydrogen, alkyl, cycloalkyl, nitro, cyano, halogen, alkoxy, acetamido, alkoxycarbonyl, aryloxycarbonyl, and aryl; the method comprising the steps of converting a corresponding compound of formula 2:

R$_1$O.OC—CHR$_2$—CO.OR$_3$     formula 2 in the presence of a base, or a salt of a compound of formula 2, into the corresponding compound of formula 1 by reaction with elemental fluorine.

2. A process as in claim 1 wherein a compound of formula 2 is converted into a salt prior to fluorination of the salt with elemental fluorine.

3. A process as in claim 1 wherein a compound of formula 2 is present with a base which does not substantially form a salt therewith during the fluorinations of the compound of formula 2 with elemental fluorine.

4. A process as in claim 1, wherein the fluorine is passed into a liquid containing the compound of formula 2 or salt thereof.

5. A process as in claim 4 wherein the fluorine is passed into a liquid containing a compound of formula 2, the liquid comprising an inert organic solvent which also includes the base.

6. A process as in claim 4 wherein the fluorine is diluted with an inert gas prior to being passed into the said liquid.

7. A process as in claim 1 wherein the ester of formula 1 has terminal groups R$_1$ and R$_3$ which are independently n-alkyl groups having from 1 to 4 carbon atoms.

8. A process as in claim 1 wherein R$_2$ is a C$_{1-6}$ alkyl.

* * * * *